(12) United States Patent
Schosnig et al.

(10) Patent No.: US 8,282,893 B2
(45) Date of Patent: Oct. 9, 2012

(54) TEST TAPE UNIT AND TEST TAPE DEVICE

(75) Inventors: Stefan Schosnig, Hirschberg-Gross-sachsen (DE); Wolfgang Heck, Frankenthal (DE); Ulrich Porsch, Weinheim (DE); Robert Lorenz, Worms (DE); Ulrich Kehr, Gartringen (DE); Andree Treinzen, Heimsheim (DE); Beda Steinacher, Wettingen (CH); Stefan Sieber, Schlieren (CH); Udo Manser, Schwetzingen (DE); Karl Miltner, Frankenthal (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/083,918

(22) Filed: Apr. 11, 2011

(65) Prior Publication Data

US 2011/0243810 A1    Oct. 6, 2011

Related U.S. Application Data

(63) Continuation of application No. PCT/EP2009/063423, filed on Oct. 14, 2009.

(30) Foreign Application Priority Data

Oct. 17, 2008 (EP) .................................... 08166955

(51) Int. Cl.
*G01N 21/75* (2006.01)

(52) U.S. Cl. ......... 422/400; 422/67; 422/66; 422/82.05; 436/44

(58) Field of Classification Search .................... 422/66, 422/67, 82.05, 400; 436/44
See application file for complete search history.

(56) References Cited

U.S. PATENT DOCUMENTS

| | | |
|---|---|---|
| 2006/0233663 A1* | 10/2006 | Harttig et al. .................. 422/58 |
| 2007/0020143 A1* | 1/2007 | Seidenstricker et al. ....... 422/56 |
| 2007/0217950 A1* | 9/2007 | Kramer et al. .................. 422/66 |

FOREIGN PATENT DOCUMENTS

| | | |
|---|---|---|
| EP | 0 779 984 B1 | 11/2001 |
| EP | 1424040 A1 | 6/2004 |
| EP | 1 710 565 | 10/2006 |
| EP | 1 739 432 | 1/2007 |
| EP | 1 785 730 | 5/2007 |
| EP | 1 990 002 | 11/2008 |
| EP | 0 299 517 | 1/2009 |
| WO | WO 2007/010087 A2 | 1/2007 |

* cited by examiner

*Primary Examiner* — Lyle Alexander
*Assistant Examiner* — Dwan A Gerido
(74) *Attorney, Agent, or Firm* — Krieg DeVault LLP

(57) ABSTRACT

A test tape unit with a flexible carrier tape that can be wound forwardly by a tape drive is provided. The carrier tape includes a plurality of analytical test fields for the application of body fluid that are each applied in an associated tape section. Each tape section has a plurality of position markers for different functional positions that can be scanned by means of a tape sensor and can thereby be individually identified by measured quantity.

21 Claims, 1 Drawing Sheet

U.S. Patent     Oct. 9, 2012     US 8,282,893 B2
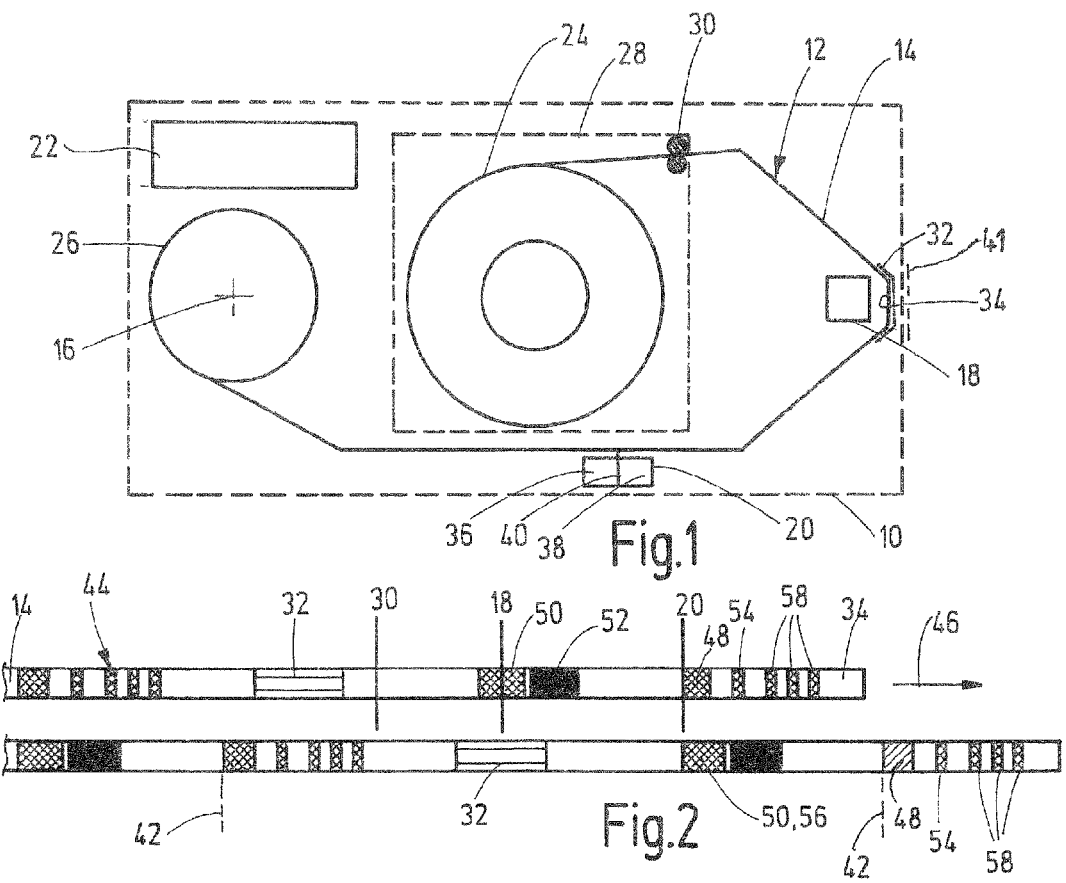
Fig.1
Fig.2
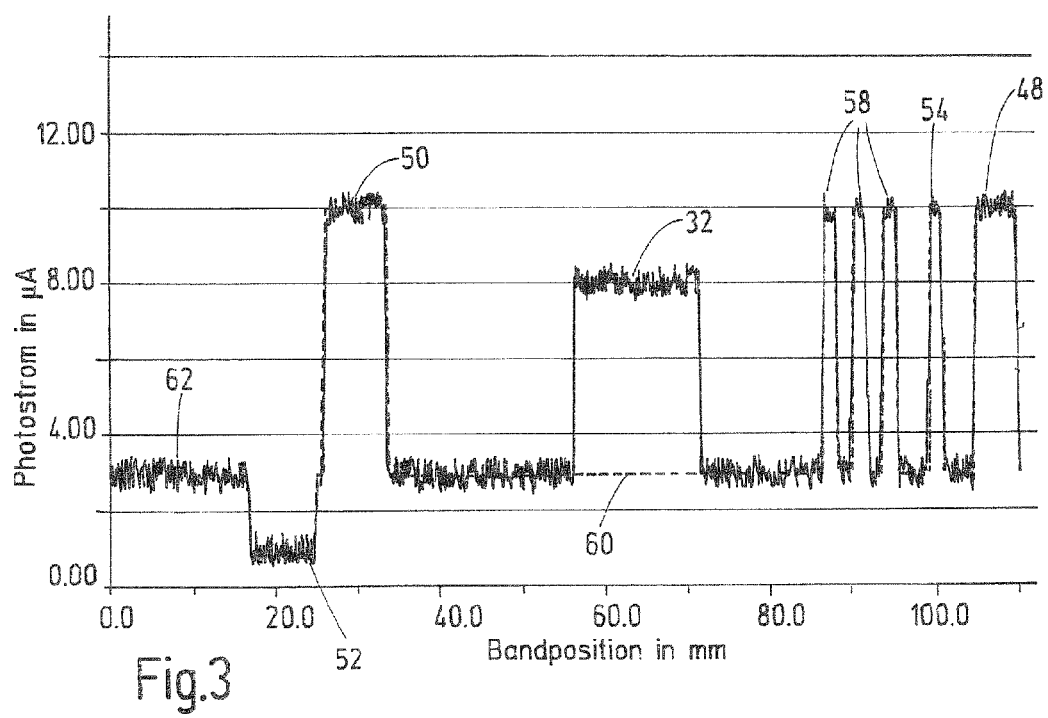
Fig.3

TEST TAPE UNIT AND TEST TAPE DEVICE

CROSS-REFERENCE TO RELATED APPLICATIONS

This application is a continuation of International Application No. PCT/EP2009/063423 filed Oct. 14, 2009, which claims priority to EP Application No. 08166955.8 filed Oct. 17, 2008. Each of the referenced applications is incorporated herein by reference in its entirety.

FIELD OF THE INVENTION

The invention concerns a test tape unit with a flexible carrier tape that can be wound forwardly by a tape drive and on which a plurality of analytical test fields are applied for the application of body fluid, such as for glucose tests, wherein a tape section is assigned to each test field. The invention further concerns a test tape device to process such a test tape unit.

BACKGROUND

A test tape unit is known from EP-A 1 739 432 of the applicants. In that case areas for determining the distance travelled are provided in the form of raster strips between the test fields which are scanned during the tape movement to determine the tape transport path wherein the corresponding signal flank alternation is added up in a counter so that the counter reading is proportional to the distance travelled by the tape. From this one can also derive a position detection, but only the rapid and exact positioning of test fields at the designated measurement site is referred to in this connection. The scanned distance increments can not, however, be differentiated from one another and hence this indirect method of position determination requires that an unnoticed change in the tape position has not taken place.

SUMMARY

On this basis the object of the invention is to further improve the systems proposed in the prior art and to ensure an increased user friendliness and functionality in the measuring process.

The invention is based on the idea of unambiguously defining different functional positions for each test by means of a tape code structure. Accordingly it is proposed that each tape section has a plurality of position markers for different functional positions that can be sensed by means of a tape sensor and can thereby be individually identified by a measured quantity. In this manner it is possible to achieve an accurate and robust tape positioning in a plurality of pre-defined positions of each tape section for a complex measuring process, where it must be taken into consideration that in a compact, in particular portable system, only an advancing drive can be implemented at acceptable costs and not a bidirectional tape transport. At the same time the pre-set sequence of the position markers that can be distinguished from one another allows a check for (unintentional) user manipulation thus increasing test reliability and preventing a loss of individual test fields or of the entire store of tests. In addition the time required to provide a test can be reduced by an advantageous positioning.

The position markers generate a distinct signal pattern for their specific sequence as a measured quantity as they pass the tape sensor due to an irregular distribution and/or different dimensions and/or different reflectivities. Hence, the position markers are distinguishable from each other and define a plurality of functional positions for each tape section provided with a test field.

Generally, the functional positions defined by the position markers can be selectively accessed by winding and eventually stopping the carrier tape. One embodiment provides that the functional positions define at least a start position and a measuring position of the test field located on the respective tape section. In this connection, when the start position marker for positioning the test field in a start position is arranged at a set distance from the test field, the test field in the start position is arranged in a storage area which is sealed against the environment. Such an additional start or resting position can, apart from the suitable storage of the sensitive test material, also enable an advantageous tape position to be adopted. For example, the next test in each case should be available to the user without a long delay while also avoiding unfavorable test field positions in the area of seals or deflecting points.

According to another embodiment, each tape section has a measuring position marker to position the test field in a measuring position, wherein body fluid can be or is applied to the test field in the measuring position.

It is possible that the position markers define the position of further functional fields besides the test field on the respective tape section. In order to further improve the accuracy of the measurement, at least one check position marker to position an assigned check field is provided on each tape section such that the check field can be scanned by a measuring unit provided to measure the test field. In this connection the size of the check field should be such that a measurement window detected by the measuring unit can be completely covered and penetration of extraneous light is avoided.

Another embodiment provides at least one position marker that has an additional function as a check field for a measuring unit. This enables a limitation of the required length of the tape sections furnished with a test field.

In another embodiment, at least one control position marker comprises a plurality of individual fields to improve the error detection.

According to another embodiment, the carrier tape includes a transparent foil material while the position markers can be formed by optically detectable fields, in particular color fields printed on the foil material.

In order to unequivocally detect the tape code structure, the measurement spot that can be resolved by the tape sensor should be smaller than the smallest position marker.

The invention also concerns a test tape device comprising a tape drive for the test tape unit that can be exchanged as a consumable unit, such as a tape cassette, a measuring unit to scan the measuring fields in a measuring position and a control device comprising the tape sensor and control software to actuate the tape drive according to the position markers.

In order to as far as possible avoid signal fluctuations due to changes in the position and material effects of the tape material, the tape sensor should have a light source and a light receiver wherein the light source and the light receiver are orientated towards the carrier tape in such a manner that essentially only diffusely reflected light is detected. For the manufacturing technology it is also advantageous when such a sensor can be mounted as a structural unit on one side of the tape transport path.

According to a further embodiment, the control device is designed in a learning phase to detect the associated signal level during scanning of the carrier tape and to determine therefrom switching thresholds for subsequently distinguishing between position markers and other areas of the tape. This results in a particular robustness of the tape positioning in even the case of potential instrument-related and tape-related manufacturing tolerances or aging effects.

Another aspect of the invention is that the control unit is designed to compare a signal pattern scanned during forwarding with a stored signal pattern of the position markers so that when a deviation is recognized as a fault, a subsequent tape section can be provided. A possible fault is, for example, a user manipulation of the tape cassette outside the device, for example, by manually rotating the take-up spool so that the tape is not in a normal position at the start.

For constructional reasons it may be advantageous when the tape sensor is arranged in a fixed instrument position at a predetermined distance along the tape transport path before or after the measuring unit or the measuring position. However, it is also basically possible that the tape sensor is also designed to be a detector for evaluating the test fields.

BRIEF DESCRIPTION OF THE DRAWINGS

The invention is further elucidated in the following on the basis of an exemplary embodiment shown in the drawings.

FIG. 1 shows an analytical test tape device in a schematic diagram.

FIG. 2 shows a tape section of a test tape in two different functional positions; and FIG. 3 shows a signal course recorded when a tape section of the test ape is scanned using a tape sensor.

DETAILED DESCRIPTION

The portable test tape device 10 shown in FIG. 1 as a portable analysis system enables the use of a test tape unit 12 comprising a test tape 14 that can be wound forwardly in the form of a tape cassette to carry out glucose tests. The general principle of the device is described in the EP Publication No. 1424040A1 which is incorporated herein by reference. In order to be able to ensure an accurate tape positioning for all functionalities, the test tape 14 is furnished with a special positioning code.

The test tape device 10 has a tape drive 16, a measuring unit 18, a tape sensor 20 and a microprocessor-aided control device 22. The tape sensor 20 is downstream of the measuring unit 18 at a predetermined distance or distance offset along the tape transport path. It can also in principle be located in front of it.

The test tape unit 12 comprises a supply spool 24 for unused test tape 14 and a take-up spool 26 for used test tape that can be coupled with the drive 16. The supply spool 24 is arranged in a storage chamber 28 which is also sealed towards the outside by means of a seal 30 in the area of the tape passage.

The test tape 14 is provided in sections with test fields 32 on the front side of which sample liquid and in particular blood or tissue fluid can be applied in the area of a deflecting tip. The analyte (glucose) is detected by a reflection-photometric measurement on the rear side using the measuring unit 18. For this purpose the test tape 14 comprises a transparent carrier or transport tape 34 on which the test fields 32 are applied as a dry reagent layer. The test fields 32 can be successively brought into use by an appropriate tape advance. In this manner it is possible to carry out multiple tests for a patient self-monitoring without having to exchange consumables.

The tape sensor 20 enables a sensory detection of the positioning code so that the tape drive can be appropriately actuated for a defined tape positioning. The tape sensor which is arranged as an assembly in a fixed position at the side of the tape guide has an LED as a light source 36 and a photodetector 38 wherein a screen 40 prevents direct light crosstalk. By means of a suitable alignment of the light source and photodetector outside the specular reflection path, essentially only the light that is diffusely reflected from the test tape 14 is detected so that a robust, reliable detection is ensured independently of the brilliance properties and positional changes of the highly flexible test tape 14.

A closable protective cover 41 protects the test tape 14 in the area of the deflecting tip when not in use. In order to simplify the handling, the device can be directly switched on or activated by opening this protective cover 41 which is for example pivoted, without requiring additional operating steps.

As shown in FIG. 2 the spaced apart test fields 32 are located individually each on an assigned tape section 42 which is additionally provided with a positioning code 44 in the form of various position markers. During tape advance (arrow 46) the position markers 44 are moved relatively to the fixed positions in the device of the seal 30, measuring unit 18 and tape sensor 20.

A start position or park position (FIG. 2 top) is defined by a start position marker 48 at the detection site of the tape sensor 20. In the start position the next unused test field 32 is in a waiting position in the storage chamber 28 which is screened from the environment. At the same time only the thin carrier tape material is situated in the seal 30 so that this is tightly sealed.

It goes without saying that the user has an interest in a rapid availability of the system. Therefore the preparation time from device activation to the time at which blood can be applied should be in a range of a few seconds. Accordingly the required tape transport path i.e. the distance between the seal 30 and the measuring site at the deflecting tip should be kept as short as possible by a suitable device architecture. In particular the storage chamber 28 should be located near to the deflecting tip and the seal 30 should be as far forward as possible in the direction of tape travel. The speed of tape travel should be in a range of 10 to 20 mm/s whereas the distance between the seal 30 and the deflecting tip should be about 25 mm and the distance between the deflecting tip and the tape sensor should be about 30 mm.

Also the sequence of position markers 44 is expediently adapted such that the preparation time is shortened as far as possible. Accordingly function and hardware tests should be reduced in this phase to a sufficient minimum amount. Such tests can also comprise checking the state of the consumable by means of suitable check fields on the carrier tape.

In the start position a white check field 50 is located at the deflecting tip in front of the measuring unit 18. The check field 50 which is printed on the carrier tape 34 like the other position markers, is dimensioned such that the measuring window detected by the measuring unit 18 is completely covered. In the same mariner it is also possible to position an upstream black check field 52 for measurement with the aid of the assigned check position marker 54 before adopting the park position.

In the measuring position shown at the bottom of FIG. 2, the test field 32 is, in accordance with FIG. 1, in front of the measuring unit 18 whereas the white check field which is at the same time a measuring position marker 56 is at the detection site of the tape sensor 20.

Three individual fields 58 which due to the two transparent interspaces can be clearly distinguished from a test field 32 to which blood has been applied, are provided as additional control position markers.

The tape code 44 described above is repeated on each tape section 42 that is furnished with a test field 32 so that at a given length of the section for example 50 tests can be stored in a tape cassette.

The position markers 44 can be identified and distinguished from one another on the basis of their irregular distribution and size when scanned by the tape sensor 20. They define as a reference on each tape section 42 several functional positions, which can be directly detected, without the need for a path measurement of the tape travel. Accordingly various functional positions such as parking (standby), checking/calibrating and measuring can be selectively accessed by means of the control unit 32. In addition it is possible to detect unintentional changes in the tape position as described below.

FIG. 3 shows the signal pattern detected by the tape sensor 20 during tape advance together with the ideal signal course (dashed line 60) assigned to the position markers. In the measuring diagram the photocurrent of the tape sensor 20 is plotted as a measured quantity versus the tape position or tape advance (the length of a tape section 42 is in this case 110 mm). Starting from the start position (cf. FIG. 2 top) the transparent carrier tape 34 is firstly detected as a signal level 62 in front of the background of the dark inside of the device. This is followed by the signals of the position markers and of the test fields at the set distances and in the given dimensions. In order to also unequivocally detect the control position marker 58 it must be ensured that the dimensions of the narrow individual fields and interspaces scanned during tape transport do not fall below the resolution of the tape sensor 20 taking into consideration all tolerances. This also includes the scanning rate as well as the response time of the tape sensor and the tape speed.

A level-learning for the tape sensor 20 is implemented in the process control. In this connection a dark field as well as a bright field signal level is recorded in a learning phase at the start of the preparation of the test field 32 and stored for the period of a test. In particular the signal level 62 of the transparent carrier tape 34 in front of the black inner wall of the housing can be detected as a dark field. However, usually the black and white check fields 52, 50 are used. Switching thresholds for this signal level are then defined for the bright/dark transition which ensure a reliable distinction between the position markers 44 and all other areas of the test tape 14. Thus, it is possible to ensure an exact positioning even in the case of any production variations or ageing processes.

The process control is designed to check the tape transport on the basis of the sequence of the position markers 44 and prevent as far as possible a major loss of test material should manipulations have occurred. In this manner faults can also be detected which are due to users manipulating the tape cassette. Such a fault is for example due to the fact that the cassette has been rotated further to such an extent that the white control field 50 is in the area of the measuring position. Since it is impossible to establish the base level, the drive is subsequently interrupted. The control unit 22 registers a lost test and moves the next white control field 50 in front of the measuring unit 18. Subsequently the test field 32 is positioned at the measuring site and the sample liquid can be applied. In this connection a spreading layer in the test field composition usually ensures that only a single coherent sample spot is formed. The signal of the twice interrupted control position marker 58 can be clearly distinguished from this so that even the case of a manipulated tape advance as far as into the area behind the test field 32 would be unambiguously detected. Finally the position marker 54 enables the black check field 52 to be measured. In each case the error handling ensures that the entire tape cassette does not have to be discarded in the case of a faulty positioning.

Although embodiments of the invention have been described using specific terms, such description is for illustrative purposes only, and it is to be understood that changes and variations obvious to the skilled artisan are to be considered within the scope of the claims that follow and their equivalents.

What is claimed is:

1. Test tape unit, comprising:
a flexible carrier tape that can be wound forwardly by a tape drive on which carrier tape a plurality of analytical test fields are applied for the application of body fluid, wherein each test field is located on an associated tape section along with at least one check field that is separate from the test field, wherein each tape section has a plurality of position markers for different functional positions of said tape section that are configured to be individually identifiable as a measured quantity by a tape sensor, wherein at least one position marker is a check position marker and is separate from the check field assigned to the check position marker on each tape section, wherein identification of the check position marker by the tape sensor is configured to indicate the check field can be scanned for a functional check by a measuring unit that also is operable to measure the test field when the carrier tape is wound forwardly from the check field.

2. Test tape unit according to claim 1, wherein the position markers generate a distinct signal pattern for their sequence as they pass the tape sensor due to at least one of an irregular distribution, different dimensions, and different reflectivities.

3. Test tape unit according to claim 1, wherein each tape section has a measuring position marker to position the test field in a measuring position, wherein body fluid can be applied to the test field in the measuring position.

4. Test tape unit according to claim 1, wherein the size of the check field is of such a dimension that a measurement window detected by the measuring unit can be completely covered.

5. Test tape unit according to claim 1, wherein at least one position marker has an additional function as a check field for the measuring unit.

6. Test tape unit according to claim 1, wherein at least one control position marker is provided for controlling advancement of the carrier tape.

7. Test tape unit according to claim 1, wherein at least one control position marker comprises a plurality of individual fields.

8. Test tape unit according to claim 1, wherein the carrier tape includes a transparent foil material and the position markers are formed by optically detectable fields.

9. Test tape unit according to claim 1, wherein the optically detectable fields include color fields printed or glued on the foil material.

10. Test tape unit according to claim 1, wherein a measurement spot that can be resolved by the tape sensor is smaller than the smallest position marker.

11. Test tape unit according to claim 1, wherein the functional positions define at least a start position and a measuring position of the test field located on the respective tape section.

12. Test tape unit according to claim 11 wherein a start position marker for positioning the test field in a start position is arranged at a set distance from the test field, wherein the test field in the start position is arranged in a storage area which is sealed against the environment.

13. Test tape device comprising:

a test tape unit including a flexible carrier tape, the carrier tape including a plurality of analytical test fields for the application of body fluid, wherein each test field is located on an associated tape section along with at least one check field that is separate from the test field, wherein each tape section has a plurality of position markers for different functional positions that are configured to be individually identifiable as a measured quantity, wherein at least one position marker is a check position marker and is separate from the check field assigned to the check position marker on each tape section;

a tape drive for the test tape unit that can be exchanged as a consumable unit in the form of a tape cassette;

a measuring unit configured to scan the check fields as a functional check and to scan the test fields in a measuring position; and a control device comprising a tape sensor configured to scan and identify the position markers to actuate the tape drive according to the position markers, wherein identification of the check position marker by the tape sensor is configured to indicate the check field is positioned for scanning as a functional check by the measuring unit.

14. Test tape device according to claim 13, wherein the tape sensor has a light source and a light receiver wherein the light source and the light receiver are orientated towards the carrier tape in such a manner that essentially only diffusely reflected light is detected.

15. Test tape device according to claim 13, wherein the control device is configured to detect associated signal levels during scanning of the carrier tape in a learning phase and to determine therefrom switching thresholds for subsequently distinguishing between position markers and other areas of the carrier tape.

16. Test tape device according to claim 13, wherein the control unit is configured to compare a signal pattern scanned during test tape forwarding with a stored signal pattern of the position markers so that when a deviation is recognized as a fault, a subsequent tape section can be provided.

17. Test tape device according to claim 13, wherein the tape sensor that detects the position markers is arranged in a fixed instrument position at a predetermined distance along the tape transport path before or after the measuring unit.

18. Test tape device according to claim 13, wherein in a start position the check field is arranged to be scanned by the measuring unit for the functional check, wherein the region of carrier tape between the check field and the next unused test field is free of position markers.

19. Test tape device according to claim 13, wherein when the test tape device is activated the tape drive is operable to provide a test field at the measuring position in less than 8 seconds.

20. Test tape device according to claim 13, wherein when the test tape device is activated the tape drive is operable to provide a test field at the measuring position in less than 3 seconds.

21. Test tape device according to claim 13, wherein a protective cover for the carrier tape when opened also forms a switch to directly switch on the test tape device.

\* \* \* \* \*